United States Patent [19]
Schnittger et al.

[11] Patent Number: 6,114,377
[45] Date of Patent: Sep. 5, 2000

[54] ANTIMICROBIAL COSMETIC COMPOSITIONS

[75] Inventors: Steven F. Schnittger, Huntington Station, N.Y.; Lieve Declercq, Ekeren, Belgium

[73] Assignee: E-L Management Corp., New York, N.Y.

[21] Appl. No.: 08/896,194

[22] Filed: Jul. 17, 1997

[51] Int. Cl.[7] .......................... A61K 31/34; A61K 31/19
[52] U.S. Cl. ............................. 514/461; 514/572
[58] Field of Search ..................... 514/461, 572

[56] References Cited

U.S. PATENT DOCUMENTS 5,387,605  2/1995  Beilfuss et al. .

FOREIGN PATENT DOCUMENTS

| 582 359 | 2/1994 | European Pat. Off. ....... A01N 43/08 |
| 582359 | 2/1994 | European Pat. Off. ....... A01N 43/08 |
| 801945 | 10/1997 | European Pat. Off. ......... A61K 7/48 |
| 2 258 836 | 8/1975 | France . |
| 2258836 | 8/1975 | France .............................. A61K 7/48 |
| 59-067211 | 4/1984 | Japan ................................ A61K 7/00 |
| 06 256137 | 9/1994 | Japan ................................ A61K 7/00 |

OTHER PUBLICATIONS

Chemical Abstract, vol. 92, No. 23 published Jun. 9, 1980; abstract No. 92:198185 "Use Of Peroxide Oxidation of Furan Aldehydes . . . " Krapivin et al.

"Study Of Antibacterial And Antiinflammatory Components Of Achillea Alpina" Journal Of Traditional Chinese Medicine, vol. 3, No. 3 published 1983, pp. 213–216 Meilan et al.

Chemical Abstracts, vol. 104, No. 11 published Mar. 17, 1986, abstract No. 104:81532 "Pharmacological Effect of the Organic Acids of Achillea Alpina" Li et al.

Action of Ferulic Acid and its Derivatives as Antioxidants, Kunio Yagi and Nobuko Ohishi, J. Nutr. Sci. Vitaminol., 25, 127–130, 1979.

The Multiactive Efficacy of Ferulic Acid in Cosmetics, Dr. Heinz Eggensperger, Chematic Consulting, Hamburg, Michele Wilker, GfN GmbH, Wald Michelbach.

Antioxidant Potential of Ferulic Acid, Ernst Graf, Free Radical Biology & Medicine, vol. 13, pp. 135–148 1992.

The Multiactive Efficacy of Ferulic Acid and its Esters in Cosmetics, Dr. Heinz Eggensperger, Michele Wilker.

Vanlllin as an Antimicrobial for Producing Shelf–Stable Strawberry Puree Patricia Cerrutti, Stella M. Alzamonia, and Susana L. Vidales—J. of Food Science, vol. 62, No. 3, 1997.

*Primary Examiner*—Zohreh Fay
*Attorney, Agent, or Firm*—Karen A. Lowney, Esq.

[57] ABSTRACT

The present invention relates to cosmetic or pharmaceutical formulations for topical application which comprises an antimicrobial effective amount of 3-furan carboxylic acid. The formulation also optionally comprises an anti-irritant effective amount of ferulic acid and an antimicrobial effective amount of 2-furan carboxylic acid.

15 Claims, No Drawings

6,114,377

ANTIMICROBIAL COSMETIC COMPOSITIONS

FIELD OF THE INVENTION

The invention relates to novel cosmetic compositions. In particular, the invention relates to cosmetic compositions having unique antimicrobial and antiirritant properties.

BACKGROUND OF THE INVENTION

Water miscible cosmetic and toiletry formulations are frequently susceptible to microbial contamination, due to their high water content and the nature of ingredients that they often contain. This is particularly true with the trend toward "natural" cosmetic ingredients, which are more likely to be susceptible to contamination than synthetic ingredients may be. The occurrence of microbial contamination in a cosmetic formulation can result in an unpleasant odor or the destabilization of an emulsion; this in turn can lead to the necessity of reformulation or recall of a commercial product.

To counteract this problem, it is often necessary to add antimicrobial chemicals, such as preservatives or biocides, to the formulation to prevent the growth of microbes that may be introduced during the manufacturing, filling or use of the product. However, such additives have recently fallen into disfavor, in large part because many preservatives are perceived as causing irritation and consumers are now demanding preservative-free products. Therefore, the market is shifting toward lower levels of conventional preservatives, and also the replacement of conventional preservatives with new molecules. Thus, there is now a strong demand for cosmetic formulations which are non-irritating and free of traditional preservatives, but which will remain stable and free of contamination in the hands of the consumer. The present invention provides such formulations.

SUMMARY OF THE INVENTION

The present invention relates to a cosmetic or pharmaceutical formulation for topical application which comprises an antimicrobial effective amount of 3-furan carboxylic acid. In a preferred embodiment, the formulation also comprises an anti-irritant effective amount of ferulic acid, or a derivative thereof. In a particularly preferred embodiment, the formulation also comprises an antimicrobial effective amount of 2-furan carboxylic acid. All such formulations are capable of being made free of preservatives, and achieve the desired effects by the use of naturally occurring materials.

The invention also relates to method for reducing the irritant effect of a cosmetic or pharmaceutical formulation comprising adding to the formulation an anti-irritant effective amount of ferulic acid or a derivative or analog thereof, as well as reducing or preventing irritation on the skin by topical application to the skin of a formulation containing ferulic acid or a derivative thereof. Also encompassed is a method for inhibiting microbial growth in a cosmetic or pharmaceutical formulation which comprises adding to the formulation an antimicrobial effective amount of 3-furan carboxylic acid.

DETAILED DESCRIPTION OF THE INVENTION

Furan carboxylic acids are naturally occurring degradation products from lignin and cellulose. 2-furan carboxylic acid has previously been disclosed as having antimicrobial activity, and has been said to be particularly effective against mycobacteria(U.S. Pat. No. 5,387,605). However, antimicrobial activity for 3-furan carboxylic acid has not previously been reported; in the context of the present invention, it has now been unexpectedly discovered that 3-furan carboxylic acid has potent antimicrobial properties. Particularly surprising is the observation that this acid has a greater level of antimicrobial activity than 2-furan carboxylic acid. In contrast with the latter, 3-furan carboxylic acid has sufficient antimicrobial activity to be used as the sole antimicrobial in a cosmetic formulation over a broad pH range. In particular, it is noted that 3-furan carboxylic acid is capable of preventing growth of Enterics, Pseudomonas, Staphylococcus and Mold, and substantially reducing the growth of yeast; in contrast, although 2-furan carboxylic acid does exhibit inhibition of Enterics, Pseudomonas, and Staphylococcus, it has a very poor level of activity against Mold and yeast, making it inadequate on its own to preserve a cosmetic formulation. To achieve the desired antimicrobial effect, 3-furan carboxylic acid alone can be used in the formulation in an amount of from about 0.05–5%, preferably 0.1–3%, by weight of the total composition. Although the 2-furan carboxylic acid alone is insufficient protection, it may be desirable to use it in combination with 3-furan carboxylic acid as a supplement to that acid's activity, in an amount of 0.5–5%. In preferred formulations of the invention, both acids are combined, and in each case, throughout the specification and the claims, when the acid is referred to, it is understood that this refers to both the free acid and derivatives thereof having the same activity. These compounds are available commercially, for example, from Sigma Chemical.

An additional useful component of the formulation is ferulic acid or derivatives thereof. Ferulic acid is also a naturally occurring material; it is found as a free acid in plants, and also occurs in ester form in seeds, leave and bark of plants. Esters are formed, for example, with long chain alcohols, sterols, and hydroxyacids. Ferulic acid has previously been said to exhibit a variety of biological activities, such as antioxidant, deodorant, antiinflammatory, antimicrobial and antipruritic. It has not, however, to the inventors' knowledge, been identified as an antiirritant. In accordance with the present invention, ferulic acid has been shown to have substantial antiirritant properties, which render it particularly useful in cosmetic formulations, and may be particularly desirable in combination with an active acid component that has the potential of causing irritation on the skin. The antiirritant effect of ferulic acid can be achieved by application shortly prior to, or simultaneously with, or shortly after exposure of the skin to an irritating material. It may also be used alone to generally soothe sensitive, easily irritated skin. As used herein, the term "ferulic acid" will be understood to encompass both the free acid and ester forms having the same activity as the free acid, unless otherwise specified. In the formulation, the ferulic acid is preferably used in an amount of from about 0.05–2.5%, more preferably 0.1–1% by weight of the total composition.

It is particularly preferred that ferulic acid, or an ester thereof, is combined with both 2-furan carboxylic acid and 3-furan carboxylic acid, in the amounts specified above for each individual component. The formulations containing this combination exhibit sufficient antimicrobial control to avoid the use of conventional cosmetic or pharmaceutical preservatives. By "conventional" preservatives is meant those preservatives which have been routinely used in the past for inhibition of microbial growth; these include, but are not limited to, parabens, propionates, formaldehyde releasers, benzoates, and cresols. An added advantage of such formulations is that they are not only inherently nonirritating, but also reduce irritation already existing on the skin to which they are applied.

In an optional embodiment, the formulations may also comprise vanillin, vanillic acid, or vanillic acid esters, in an amount of from about 0.05–1%. Vanillin is also a naturally occurring material, which is known to have activity as an antimicrobial(Principles and Practice of Disinfection, Preservation and Sterilization, Russell et al, eds., Second Edition, Blackwell Scientific Publications; Cerrutti et al., J. Food Sci. 62: 608–610, 1997.)

For topical application, the active components can be formulated with a variety of cosmetically and/or pharmaceutically acceptable carriers. The term "pharmaceutically or cosmetically acceptable carrier" refers to a vehicle, for either pharmaceutical or cosmetic use, which vehicle delivers the active components to the intended target and which will not cause harm to humans or other recipient organisms. As used herein, "pharmaceutical" or "cosmetic" will be understood to encompass both human and animal pharmaceuticals or cosmetics. Useful carriers include, for example, water, acetone, ethanol, ethylene glycol, propylene glycol, butane-1, 3-diol, isopropyl myristate, isopropyl palmitate, or mineral oil. Methodology and components for formulation of cosmetic and pharmaceutical compositions are well known, and can be found, for example, in Remington's Pharmaceutical Sciences, Eighteenth Edition, A. R. Gennaro, Ed., Mack Publishing Co. Easton Pa., 1990. The carrier may be in any form appropriate to the mode of delivery, for example, solutions, colloidal dispersions, emulsions(oil-in-water or water-in-oil), suspensions, creams, lotions, gels, foams, mousses, sprays and the like. The pH for the formulations of the invention can be from about 3 to about 8, preferably about 4–7, and most preferably about 4–6.

The formulation, in addition to the carrier and the antimicrobial/antiirritant components, also can comprise other optional materials which may be chosen depending on the carrier and/or the intended use of the formulation. Additional components include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like.

The antimicrobial/antiirritant components are well-suited for combination with other active components intended for topical application. In particular, the ferulic acid may assist in reducing the irritating effects of other active components in a formulation. Examples of known irritants that are frequently used for therapeutic purposes topically are retinoids, such as retinol and retinoic acid, and hydroxyacids, such as glycolic, lactic, or salicylic acids. Examples of other types of actives which may form part of the composition include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, skin lightening agents, depigmenting agents, wound-healing agents, vitamins, corticosteroids, tanning agents, sunscreens or hormones. More specific examples of useful active agents include retinoids, topical cardiovascular agents, clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, retinol, retinoic acid, 13-cis retinoic acid, hydrocortisone, hydrocortisone 21-acetate, hydrocortisone 17-valerate, hydrocortisone 17-butyrate, betamethasone valerate, betamethasone diproprionate, triamcinolone acetonide, fluocinonide, clobetasol, proprionate, benzoyl peroxide, crotamiton, propranolol, promethazine, vitamin A palmitate, vitamin E acetate, DHEA and derivatives thereof, alpha- or beta-hydroxy acids, and mixtures thereof. The amount of active agent to be used in any given formulation is readily determined in accordance with its usual dosage.

Particularly preferred embodiments of the present formulations are moisturizing creams or lotions. To that end, the antimicrobials/antiirritant components are combined with agents that are moisturizers, emollients or humectants. Examples of useful combinations are oils, fats, waxes, esters, fatty acid alcohols, fatty acid ethoxylates, glycols, sugars, hyaluronic acid and hyaluronates, dimethicone, cyclomethicone, and the like. Further examples can be found in the International Cosmetic Ingredient Dictionary, CTFA, Sixth Edition, 1995. The invention is further illustrated by the following non-limiting examples.

Application of the formulations of the invention is achieved in accordance with the nature and intended use of the final product. For example, a moisturizing, cleansing, or skin-soothing formulation may be used on a daily basis, or more or less frequently depending upon need. If the formulation contains a pharmaceutical or cosmetic active, the application will be in accordance with the recommended regimen for the active. Determination of Other Appropriate Application Regimens is a Matter of Routine Optimization.

EXAMPLES

I. This example illustrates the efficacy of 3-furan carboxylic acid in retarding microbial growth in a cosmetic formulation.

A nonionic oil-in-water emulsion is prepared containing 0.473% 3-furan carboxylic acid. The formulation is divided into five portions, each one getting an inoculation at day 0, and a reinoculation after three weeks, of one of the following microbial cultures: (1)Enterics; (2)Pseudomonas; (3)Staphylococcus; (4)Yeast; and (5)Mold. The concentration of microbes in each individual formulation is calculated on the day of the inoculation, and then again calculated on day 2, and at the end of one, two, three(pre-reinoculation) and four weeks, at a variety of pH values. These are also compared with formulations containing 2-furan carboxylic acid and an identical series of microbes, and an acid pH control emulsion without a furan carboxylic acid added. The results are shown in Tables 1, 2 and 3. All numbers, other than those listed as "<10", are log base 10; thus, for example, "6.6" is equivalent to the presence of 8 million bacteria. Entries of <10 indicate less than 10 colony forming units, the lowest level of detection.

TABLE 1

0.473% 3-furan carboxylic acid

| Pool # | Day 0 | Day 2 | Week 1 | Week 2 | Week 3 | Week 4 |
|---|---|---|---|---|---|---|
| A. pH 3.0 | | | | | | |
| 1 | 6.6 | <10 | <10 | <10 | <10 | <10 |
| 2 | 6.3 | <10 | <10 | <10 | <10 | <10 |
| 3 | 6.3 | <10 | <10 | <10 | <10 | <10 |
| 4 | 5.7 | <10 | <10 | <10 | <10 | <10 |
| 5 | 5.2 | <10 | <10 | <10 | <10 | <10 |
| B. pH 4.0 | | | | | | |
| 1 | 6.6 | <10 | <10 | <10 | <10 | <10 |
| 2 | 6.3 | <10 | <10 | <10 | <10 | <10 |
| 3 | 6.3 | <10 | <10 | <10 | <10 | <10 |
| 4 | 5.7 | 2.5 | <10 | <10 | <10 | <10 |
| 5 | 5.2 | <10 | <10 | <10 | <10 | <10 |
| C. pH 5.0 | | | | | | |
| 1 | 6.6 | <10 | <10 | <10 | <10 | <10 |
| 2 | 6.3 | <10 | <10 | <10 | <10 | <10 |
| 3 | 6.3 | <10 | <10 | <10 | <10 | <10 |
| 4 | 5.7 | 2.5 | 2.7 | 1.7 | 2.0 | 1.8 |
| 5 | 5.2 | <10 | <10 | <10 | <10 | <10 |

TABLE 2

0.375% 2-furan carboxylic acid

| Pool # | Day 0 | Day 2 | Week 1 | Week 2 | Week 3 | Week 4 |
|---|---|---|---|---|---|---|
| A. pH 3.0 | | | | | | |
| 1 | 6.6 | <10 | <10 | <10 | <10 | <10 |
| 2 | 6.3 | <10 | <10 | <10 | <10 | <10 |
| 3 | 6.3 | <10 | <10 | <10 | <10 | <10 |
| 4 | 5.7 | <10 | <10 | <10 | <10 | <10 |
| 5 | 5.2 | <10 | <10 | <10 | <10 | <10 |
| B. pH 4.0 | | | | | | |
| 1 | 66 | <10 | <10 | <10 | <10 | <10 |
| 2 | 6.3 | <10 | <10 | <10 | <10 | <10 |
| 3 | 6.3 | <10 | <10 | <10 | <10 | <10 |
| 4 | 5.7 | 3.7 | 3.7 | <10 | <10 | >5.7 |
| 5 | 5.2 | 1.6 | <10 | <10 | <10 | <10 |
| C. pH 5.0 | | | | | | |
| 1 | 6.6 | >6 | >6 | <10 | <10 | <10 |
| 2 | 6.3 | >6 | <10 | <10 | <10 | <10 |
| 3 | 6.3 | 2.9 | <10 | <10 | <1D | <10 |
| 4 | 5.7 | >5.7 | >5.7 | >5.7 | >5.7 | >5.7 |
| 5 | 5.2 | 5.2 | 5.2 | 5.2 | 3.0 | >5 |

TABLE 3

Control emulsion

| Pool # | Day 0 | Day 2 | Week 1 | Week 2 | Week 3 | Week 4 |
|---|---|---|---|---|---|---|
| A. pH 3.0 | | | | | | |
| 1 | 6.6 | 3.7 | <10 | <10 | <10 | <10 |
| 2 | 6.3 | >6 | <10 | <10 | <10 | <10 |
| 3 | 6.3 | 2.0 | <10 | <10 | <10 | <10 |
| 4 | 5.7 | 5.7 | 5.7 | 5.7 | 4.5 | >6 |
| 5 | 5.2 | 5.2 | 5.2 | 5.2 | 5.2 | >5 |
| B. pH 4.0 | | | | | | |
| 1 | 6.6 | >6 | >6 | 3.2 | <10 | >6 |
| 2 | 6.3 | >6 | >6 | <10 | <10 | <10 |
| 3 | 6.3 | >6 | 2.0 | 2.0 | <10 | <10 |
| 4 | 5.7 | >6 | >6 | >6 | >6 | >6 |
| 5 | 5.2 | 5.2 | 5.2. | 5.2 | 3.3 | >5 |
| C. pH 5.0 | | | | | | |
| 1 | 6.6 | >6 | >6 | >6 | 2.0 | >6 |
| 2 | 6.3 | >6 | >6 | <10 | <10 | <10 |
| 3 | 6.3 | >6 | >6 | >6 | 4.2 | <10 |
| 4 | 5.7 | >6 | >6 | >6 | >6 | >6 |
| 5 | 5.2 | >5.2 | 5.2 | 5.2 | 3.0 | >6 |

Comparison of the antimicrobial effects of the two furan carboxylic acids shows that the 3-furan carboxylic acid is superior to 2-furan carboxylic acid in its ability to retard the growth of mold and yeast. The control shows that the antimicrobial effect of these two acids is due to the characteristics of the specific acid, rather than the acid pH or the vehicle used.

EXAMPLE 2

This example illustrates the antiirritant effect of the components of the invention:

Seven volunteers with a history of skin sensitivity to Balsam of Peru are chosen for the study. The test compounds studied are as follows: Ferulic acid, 0.1% in hydroalcohol 1:1; 2-furan carboxylic acid, 0.1% in hydroalcohol 1:1; and 3-furan carboxylic acid, 0.1% in hydroalcohol, 1:1.

The test compounds are applied to the ventral forearms of panelists. The material is allowed to absorb for twenty minutes and then Balsam of Peru, an irritant is applied on the test sites. Skin irritation is measured in terms of increase in skin redness. The degree of redness is measured with a Minolta Chromameter and compared with the controls, the positive control being skin treated with Balsam of Peru alone, and the negative control being a skin site treated with 10% cola solution(a known antiirritant), and challenged like the test products.

Ferulic acid is 72% effective in preventing the onset of irritation. This compares favorably with the cola solution, which shows 69% reduction. Interestingly, both 2- and 3-furan carboxylic acid show some reduction in the onset of irritation, at 49% and 48%, respectively.

What we claim is:

1. A cosmetic or pharmaceutical formulation for topical application, the formulation comprising an antimicrobial effective amount of 3-furan carboxylic acid, combined with an antimicrobial effective of 2-furan carboxylic acid.

2. The formulation of claim 1 which comprises an antiirritant effective amount of ferulic acid.

3. The formulation of claim 1 in which the acid is in free acid form.

4. The formulation of claim 1 which also comprises vanillin.

5. The formulation of claim 2 which also comprises vanillin.

6. The formulation of claim 1 which is a moisturizing formulation.

7. The formulation of claim 2 which is a moisturizing formulation.

8. The formulation of claim 1 in which the amount of acid is from about 0.5–5%.

9. The formulation of claim 2 which comprises from 0.5–5% of each of free 2-furan carboxylic acid and 3-furan carboxylic acid, and from 0.5–2.5% of free ferulic acid.

10. A preservative-free cosmetic or pharmaceutical formulation comprising antimicrobial effective amounts of 3-furan carboxylic acid and 2-furan carboxylic acid, and an antiirritant effective amount of ferulic acid.

11. The formulation of claim 10 in which each of the acids is in free acid form.

12. A method for retarding microbial growth in a cosmetic or pharmaceutical formulation which comprises adding to the formulation an antimicrobial effective amount of 3-furan carboxylic acid.

13. A method for retarding microbial growth on skin which comprises applying to the skin an effective amount of a formulation comprising an antimicrobial effective amount of 3-furan carboxylic acid.

14. The method for retarding microbial growth on skin which comprises applying to the skin an effective amount of a formulation of claim 2.

15. The method for retarding microbial growth on skin which comprises applying to the skin an effective amount of a formulation of claim 9.

\* \* \* \* \*